United States Patent [19]

Cunningham et al.

[11] Patent Number: 5,310,469
[45] Date of Patent: May 10, 1994

[54] BIOSENSOR WITH A MEMBRANE CONTAINING BIOLOGICALLY ACTIVE MATERIAL

[75] Inventors: David D. Cunningham, Lakemoor; Susan B. Brontman, Buffalo Grove; Jill M. Geist, Ingleside; R. Hayes Helgren, Mundelein; Timothy P. Henning, Vernon Hills; Kenneth S. Johnson, Buffalo Grove; Laura S. Morici, Cary, all of Ill.; Thomas G. Schapira, Bristol; Neal T. Sleszynski, Kenosha, both of Wis.

[73] Assignee: Abbott Laboratories, Abbott Park, Ill.

[21] Appl. No.: 815,423

[22] Filed: Dec. 31, 1991

[51] Int. Cl.[5] ............................. G01N 27/26
[52] U.S. Cl. ........................ 204/403; 204/414; 204/415; 204/416; 204/418; 435/817; 435/288
[58] Field of Search ............... 204/403, 414, 415, 416, 204/418, 153.12; 435/288, 817

[56] References Cited

U.S. PATENT DOCUMENTS

| | | | |
|---|---|---|---|
| 3,835,014 | 9/1974 | Huffines, Jr. | 204/415 |
| 4,073,713 | 2/1978 | Newman | 204/415 |
| 4,240,889 | 12/1980 | Yoda et al. | 204/415 |
| 4,276,141 | 6/1981 | Hawkins | 204/1 T |
| 4,321,123 | 3/1982 | Nakamura et al. | 204/403 |
| 4,376,689 | 3/1983 | Nakamura et al. | 204/403 |
| 4,388,166 | 6/1983 | Suzuki et al. | 204/403 |
| 4,415,666 | 11/1983 | D'Orazio et al. | 204/403 |
| 4,454,007 | 6/1984 | Pace | 204/416 |
| 4,486,292 | 12/1984 | Blackburn | 204/416 |
| 4,549,951 | 10/1985 | Knudson et al. | 204/416 |
| 4,579,642 | 4/1986 | Niiyama et al. | 204/403 |
| 4,713,165 | 12/1987 | Conover et al. | 204/403 |
| 4,759,828 | 7/1988 | Young et al. | 204/403 |
| 4,808,529 | 2/1989 | Doppelfeld et al. | 435/179 |
| 4,889,612 | 12/1989 | Geist et al. | 204/416 |
| 4,894,339 | 1/1990 | Hanazato et al. | 204/403 |
| 4,895,806 | 1/1990 | Le et al. | 435/288 |
| 4,923,586 | 5/1990 | Katayama et al. | 204/403 |

FOREIGN PATENT DOCUMENTS 2194843A 3/1988 United Kingdom.

Primary Examiner—John Niebling
Assistant Examiner—Bruce F. Bell
Attorney, Agent, or Firm—Robert E. Wexler

[57] ABSTRACT

A sensor for measuring the concentration of an analyte in a solution is disclosed. The sensor may be adapted for use as either an amperometric or a potentiometric sensor. It includes a membrane having a biologically active protein immobilized within. The membrane is attached and reliably sealed to a housing by means of ultrasonic welding, either directly or indirectly. Further, the membrane may be compressed to a fraction of its original dimensions. Metallic parts of the device may, optionally, be physically isolated from the sample solution to reduce corrosion. These features operate synergistically so that the claimed device exhibits relatively fast response and recovery times, is reliably leak-proof, and may be constructed in relatively small sizes.

23 Claims, 4 Drawing Sheets

BIOSENSOR WITH A MEMBRANE CONTAINING BIOLOGICALLY ACTIVE MATERIAL

FIELD OF THE INVENTION

The invention relates generally to a sensor for electrochemical analysis of a catalyzed reagent in solution. More particularly, the invention relates to a sensor having a membrane in a substantially planar configuration that contains an enzyme, an antibody, or a cell culture which exhibits relatively high catalytic activity for converting a reagent to be measured into a product which can influence an electrical signal related to the sensor.

BACKGROUND OF THE INVENTION

Biosensors are electrodes which employ enzymes or other biologically active materials as highly selective catalysts. Early biosensors contained an enzyme in aqueous solution which was held in proximity to a sensing electrode by a membrane which did not contain a significant amount of the enzyme. The membranes of these biosensors served primarily as a physical barrier which, by virtue of their small pore size, prevented the enzyme from migrating into the bulk solution. The membrane also served to keep large protein molecules from entering the aqueous enzyme solution and interfering with planned reactions. These biosensors were comparatively large and their reaction times were slow by modern standards.

One improved type of biosensor held an enzyme trapped between two or more individual membranes. The enzyme could be dispersed in an adhesive which held the membranes in place, especially when the enzyme was glucose oxidase and the adhesive was glutaraldehyde. The restraining membranes did not contain a significant amount of enzyme.

Another type of biosensor contains enzymes immobilized directly within a permeable or semipermeable carrier. The enzyme may be physically encapsulated within the membrane in the form of fine droplets dispersed in a polymer. Alternately, the enzyme may be covalently bonded to functional polar groups which are attached to a synthetic polymer membrane. Functional groups include covalent binding groups, ionic binding groups, and hydrophobic groups. The immobilized enzyme membranes contain micropores which facilitate diffusion of target reagents and reaction products through the membrane.

Covalent bonds for immobilizing proteins are formed by linking amino or carboxyl groups, which are present in every enzyme, with polar functional groups which may be present on the carrier membrane. The functional groups can be derived from components normally present in the materials that forms a carrier substrate or the functional groups can be added to the carrier substrate. Suitable functional groups include carboxyl groups, amino groups, sulfonic acid groups, imino groups, thio groups, hydroxyl groups, pyridyl groups, and phosphoryl groups. The functional groups may be preactivated by chemical treatment to enhance their ability to join with the amino or carboxyl groups present in the enzyme molecules.

As biosensor technology progressed, laminated membranes were produced which included an enzyme membrane which carried immobilized proteins and other membranes. The other membranes are located on one or both sides of the enzyme membrane and serve to impede the movement of undesirable species. For example, protecting membranes having relatively large pores are included in laminated membranes between an analyte solution and an enzyme membrane in that position, the protecting membranes prevent high molecular weight species from becoming adsorbed upon and fouling the surface of the enzyme membrane. Similarly, blocking membranes with relatively smaller pores were included between the enzyme membrane and a sensing electrode to prevent low molecular weight species, such as ascorbic acid and paracetamol from interfering with electrical detection and measurement as the sensing electrode. Some of the laminated membranes are prepared by the technique of spin casting successive layers of polymeric material.

The laminated membranes are not entirely satisfactory, however. They are expensive and time-consuming to prepare. Achieving a uniform distribution of enzyme attachment within the enzyme membrane is problematic. In addition, the laminated membranes frequently leak at their point of attachment to a sensor device and an analyte solution is then able to bypass the enzyme. Laminated membranes can also separate during operation.

Accordingly, improved laminated membranes and improved methods of manufacturing have been sought, as well as substitutes. One substitute is a blocking layer deposited directly upon the sensing electrodes. Such blocking layers are produced by polymerizing compounds directly on the electrodes, such as diaminobenzene and dihydroxybenezene copolymers. Intimate contract is achieved between the sensing electrode and the blocking membrane, but the quality of devices produced by this technique is often inconsistent.

Over the last two decades, evolution in biosensor design has been stimulated by a demand for smaller, faster, and more reliable leak-proof sensors which exhibit high sensitivity. Such sensors are especially useful for constructing arrays which contain many sensors. The demand for small biosensors with faster response and recovery times appeared to be at odds with the requirements of leak-proof reliability and high sensitivity. Generally, the route to faster response times is by incorporation of more sophisticated, less diffusion-resistant membranes, and through improved immobilization techniques which uniformly distribute the enzyme in well-defined layers without exposing the enzyme to conditions which might denature it.

In contrast, the use of sophisticated membranes and advanced immobilization techniques places a premium on the integrity of a seal between the enzyme membrane and the housing. Previously, the seal had been made using clamps, mechanical fasteners, or adhesives, and was a frequent source of leakage. Leakage around the enzyme would reduce the sensitivity of the biosensor device because reagents which had not been converted would not register at the electrode. Of course, the leakage bypass problem is most critical for small biosensor devices where the deleterious effect of any given size leak becomes relatively more important. When the seal leaks, the time required to rinse out a sample or calibrant solution is extended. Avoiding leaks is especially important in the case of systems with multiple sensors.

SUMMARY OF THE INVENTION

The present invention is directed to a biosensor device which exhibits a faster response time and a faster recovery time than previous devices while maintaining high sensitivity and reliability. The new biosensor device may be adapted for use as either an amperometric sensor or a potentiometric sensor and employs a membrane that contains catalytically selective protein molecules, such as enzymes or antibodies, which react selectively with an analyte.

Good control over the attachment and distribution of the protein molecules within the membrane is achieved by immobilizing the protein on the membrane. The protein may be immobilized either before or after the membrane is assembled within a housing of the biosensor device. A permanent leak-proof connection between the enzyme membrane and the housing is achieved by welding the membrane to the housing, preferably by application of ultrasonically induced heat. The membrane may, optionally, be compressed to decrease a diffusion resistance which the membrane exhibits toward the analyte. The biologically active enzyme within the membrane is not denatured by such compression or by such welding.

In addition to the membrane containing immobilized protein molecules, a protective membrane may be installed flush with an external surface of the housing to present a simple profile to sample stream flow. The simple flow profile minimizes dead volume and backmixing of the sample, making the device suitable for use in a semi-automatic analyzer having programmed flow switching or for in vivo use within the human body. In either case, the membrane is securely attached to the housing by ultrasonic welding or sonic welding, without such mechanical fastenings as O-rings or strength-reducing adhesives. The device can be reproducibly constructed in extremely small sizes that minimize diffusion path lengths and contribute to quick response and rapid signal recovery for one sensor or an array of sensors.

In one embodiment, the device comprises an electrically insulating housing which includes a first aperture, a second aperture, and a passage that extends from the first aperture through the housing to the second aperture. The housing is impervious to a solution that contains a reagent selectively catalyzed by an enzyme. The device also comprises means for conducting electrical current which extend through the first aperture into the passage and seal against the first aperture in a manner that prevents fluid flow. Non-metallic, electrically-conductive isolating means for physically isolating the conductive means may, optionally, be provided which contact with said conducting means and cover the conducting means in a manner that physically isolates the conducting means from the passage.

An enzyme membrane is located across the passage such that the solution must pass from the second aperture through the enzyme membrane in order to contact the conducting means or, alternatively, isolating means. The membrane has a compressed substrate including an internal surface which defines a plurality of micropores distributed throughout the substrate. A plurality of functional groups are attached to the internal surface of said substrate and a plurality of biologically active material molecules are covalently or ionicly attached to at least a portion of the functional groups. The substrate may be compressed.

In another embodiment, the invention is a reusable biosensor device for measuring the concentration of an enzyme catalyzed reagent in solution which comprises (a) an electrically conducting pin having one or more side surfaces, a transmitting surface, and a receiving surface; (b) a non-porous electrically-insulating housing which is impervious to the solution and which covers the side surfaces and extends beyond the side surfaces so as to define a well that is in fluid communication with the receiving surface; (c) an ionophore gel inside the well which coats the receiving surface; (d) an enzyme membrane welded to the housing so that the enzyme membrane, the housing, and the receiving surface completely surround the ionophore gel so that the solution must pass through the enzyme membrane to contact the ionophore gel; and (e) a substantially planar membrane which covers the enzyme membrane and presents a simple flow profile to the solution. It is preferred that the means for conducting electrical current contact the enzyme membrane.

In yet another embodiment, the invention is a device for measuring the concentration of an enzyme-catalyzed reagent in solution. The apparatus comprises an electrically conductive pin. A receiving surface of the pin collects electrical information which is indicative of the concentration of the reagent in solution. A blocking layer may, optionally, extend across the receiving surface. The sides of the pin, but not the receiving surface or blocking layer, are hydraulically sealed against a thermoplastic polymer molded housing which is disposed about the pin.

An enzyme membrane containing an immobilized enzyme is ultrasonically welded to the housing, so that the enzyme-catalyzed reagent must travel through the enzyme membrane in order to contact the receiving surface of the pin. The enzyme membrane is in intimate contact with the receiving surface or the blocking layer. A substantially planar protecting membrane covers the enzyme membrane.

BRIEF DESCRIPTION OF THE DRAWINGS

FIG. 2 is an elevation view of the device of

DETAILED DESCRIPTION OF THE PREFERRED EMBODIMENTS

Figure 1:
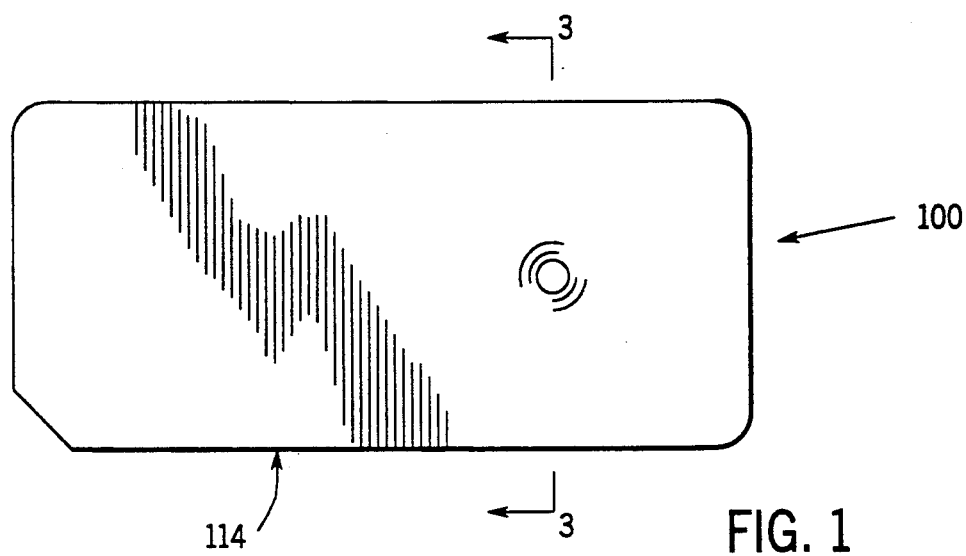
FIG. 1 is a plan view of an embodiment of the present invention.

The present invention decreases response times and recovery times required for measurement of the concentration of an analyte in solution, as compared to prior art devices. The invention is a bio-sensor device which includes a membrane which is attached to a housing by a leak-resistant welding process which does not denature biologically active materials, such as catalytically selective proteins and nucleic acid derivatives, and which is well-suited to fabrication in small sizes. Miniaturization further improves response time because diffusion paths are shorter and the device contains less dead volume for sample flow. Ultrasonic welding or solvent welding is used to attach the enzyme membrane to the housing in order to minimize leakage around the enzyme membrane and maximize enzyme utilization.

The housing of the device is impervious to a solution to be analyzed and is electrically insulating. It is preferred that the housing be constructed of a thermoplastic polymer such as polyethylene, acrylonitrile butadiene styrene (ABS), polyvinyl chloride (PVC), cellulose acetate butyrate (CAB), vinylidene chloride, fluorocarbons, polycarbonates, polypropylenes, nylons, and acetals. Especially preferred are Zylar 90# and acrylics in general. Zylar 90# is a methyl methacrylate butadiene styrene terpolymer produced by Polysar of Madison, Connecticut. These thermoplastic polymers can be injection molded around solid conductors, metallic and otherwise, to produce a conductor housing seal which is durable and highly leak-proof.

The housing has two apertures on its external surface which are connected by an internal passage. A conductor will be inserted into one of the apertures to lead an electrical signal from the passageway through the housing to the outside. There, the electrical signal can be picked up by a sensing lead and further analyzed. Because the passage will be filled with an electrolytic solution during operation, it is important that the housing be electrically insulating and that the conductor passing through the first aperture be tightly sealed against the aperture to prevent the solution from flowing toward a sensing lead and other peripheral equipment. In most cases, the seal produced by injection-molding will be sufficient.

The conductor which carries an electrical signal from the passageway through the first aperture may be metallic. Materials other than metals, such as carbon rods, have been used for similar service, but metal conductors appear to provide superior results when the device is small in size. In this specification, the term "pin" will refer to a metallic conductor which leads electrical current to the first aperture. Such a pin will have two active surfaces. The surface of the pin which faces away from the enzyme membrane will be used to pass an electrical signal to other equipment. It is called the transmitting surface. Side surfaces which contact or face the housing are not active surfaces and merely serve to make a seal with the housing against the sample solution. The other active surface is the receiving surface which will receive an electrical signal from the passage. Often, the electrical signal will be in the form of a change of current during a period when a substantially constant voltage is maintained across an amperometric device. Alternately, the signal may be a difference in electrical potential.

A recurring problem in electrochemical sensor devices having a metallic conductor is corrosion of the conductor by the electrolytic sample solution. In one form, as a potentiometric sensor, the present invention overcomes this difficulty by physically isolating the pin from the solution with a non-metallic, electrically conductive coating. It is preferred that the coating have an organic matrix, and it is most preferred that the coating include a substantial proportion of graphite. Such a layer of graphite may be screen-printed on the pin or painted upon the pin in the form of a acceptable graphite ink. Many forms of carbon are suitable for this application. One example of a suitable graphite ink is a flexible carbon keyboard contact ink offered by Minico Inc. under the tradename M-3000-RS.

The isolating inorganic matrix layer must completely cover the receiving surface which would otherwise be exposed to the electrolytic sample solution. The layer may coat other surfaces of the pin. For instance, one might dip an entire end of the pin into a pool of graphite ink to be sure that the receiving surface was fully coated. For the purposes of the present invention, a portion of the isolating organic matrix layer may extend over the side surfaces of the pin and still be within the scope of the claims.

The non-metallic conductive material may include graphite in a binding matrix or may include a conductive polymer such as polyacetylene and polypyrrole. When graphite is used, conductive carbon graphite particles can be dispersed in a blend of polymer and solvent. This dispersion is applied to electrically insulating planar surfaces by various processing techniques, such as thick or thin film patterning. It may also be dip- or spray-coated over wires or other non-planar surfaces.

The solvent is chosen to solubilize the polymer binder so that the graphite may be uniformly dispersed. The solvent is removed from the system by drying. Desirable polymers are those which adhere to the graphite particles and bind them tightly in the matrix after the solvent evaporates.

The isolating graphite layer may be used directly as an ion-selective electrode surface in applications where long leads are not required to connect the ion-selective electrode to other equipment. If long leads are necessary, the metallic pin with a protecting organic matrix layer should be employed and the leads can be connected to the pin. In some cases, it may be desirable to employ a gate area of a field-effect transistor in place of the metallic pin. Such variations are intended to be within the scope of the instant claims.

The present invention may, optionally, include a membrane having a compressed substrate containing immobilized enzyme. Surprisingly, compression of the substrate makes the enzyme inside the enzyme membrane more reactive. The immobilized enzyme which is located within internal micropores of the substrate is subject to less diffusion resistance toward specific reagents when the carrier is in a compressed state. Even though access to some of the enzyme in the carrier substrate may be restricted by the collapse of some connecting micropores, compression of the carrier increases overall mass transfer to and from the enzyme, thereby decreasing response time for the biosensor device and decreasing recovery time.

Diffusion resistance inside the substrate is a critical factor in the apparent activity of enzymes immobilized in the enzyme membrane. Therefore, a decrease in apparent diffusion resistance will decrease response time and recovery time exhibited by a biosensor device. Conversely, biosensors having more diffusion resistance toward target substrate molecules will exhibit longer response times and longer recovery times.

The porous substrate is preferably in the form of a flat sheet. It is especially preferred that the substrate is a portion of a porous semipermeable membrane made from synthetic polymer material. The membrane desirably is a thin, flexible layer.

The substrate may be composed of any compressible solid which possesses a large number of internal micropores upon which functional groups may be attached and which can exist in a compressed state and an uncompressed state. The micropores of the substrate need not be cylindrical in shape. The invention is applicable to substrates having micropores which are tortuous or sponge-like in shape. The phrase "compressed state" means that the substrate has been physically compressed between inelastic surfaces, for example, with the result that external dimensions of the substrate are reduced with respect to an uncompressed state. The uncompressed state is the state in which the membrane was originally manufactured. It is preferred that the membrane remain reversibly compressed after pressure is applied and released.

An especially preferred substrate is made from polyamide resins, in particular, copolymers of hexamethylene diamine and adipic acid (Nylon 66), copolymers of hexamethylene diamine, and sebacic acid (Nylon 610), and homopolymers of poly-E-caprolactum (Nylon 6) are preferred. In a typical process for manufacturing such membranes, the polyamide resin is dissolved in a solvent such as formic acid and a non-solvent such as water is added under controlled conditions of agitation to achieve nucleation of the solution. The nucleated solution is then cast onto a solid sheet or web in the form of a film. This film is contacted and diluted by a liquid non-solvent system. The polyamide resin thereupon precipitates forming a membrane sheet which can be washed to remove the solvent liquid. The membrane can then be stripped from the solvent sheet. Alternatively, if the sheet is porous it can be incorporated in the membrane to serve as a permanent support.

The most useful membranes are those which have a pore size in the range of about 0.01 micron to about 10 microns, where a micron is defined as $1 \times 10^{-6}$ meter. The range of about 0.1 to about 2 microns is especially preferred. The ratio of the total volume of internal micropores expressed as a percentage of the total volume of the substrate is defined as the percent porosity of the substrate. It is preferred that the substrate be in the range of about 30% porous to about 80% porous in its uncompressed state. Useful substrates in the compressed state are typically in the range of about 10% porous to about 60% porous. In practice, the membrane containing immobilized enzyme may be utilized in tandem with one or more other membranes which may possess different physical and diffusion characteristics.

The density of the substrate in its compressed state is in the range of about 1.25 to about 5.0 times the density of the substrate in an uncompressed state. The uncompressed state is defined as the state in which the porous carrier is originally manufactured. For a polymer membrane this would usually be the state existing after the membrane had been washed and dried. However, if the membrane is compressed while it is in contact with a liquid, such as a stabilizing solution which avoids denaturing the enzyme, then the compression factor should be calculated on wet membrane dimensions before and after compression.

The compressed state is achieved by physically pressing upon the membrane in its uncompressed state. Preferably, two inelastic flat surfaces are used to compress the carrier and the resulting form of the compressed carrier is a flat sheet with a thickness less than that of the uncompressed carrier. It is believed that compression of the membrane decreases the time required for diffusional processes to a new value which is proportional to the ratio of the squares of a new and an old diffusion path length.

During compression, the percent porosity of the carrier substrate decreases, typically, to a value which is about one-half that of the percent porosity in the uncompressed state. It is believed that some internal micropores are crushed or constricted by the compression. However, it appears that the length of other diffusion paths from enzyme-active sites to the external surface of the membrane are effectively decreased. A net decrease in overall diffusional resistance through the substrate is observed.

In a preferred embodiment, the substrate is only compressed in one dimension, that is, its cross-sectional dimension in sheet form. In that case, the thickness of the substrate in the compressed state should be in the range of about 0.2 to about 0.8 times the thickness of the substrate in the uncompressed state. As an illustrative example, for a membrane in sheet form that had a thickness of 145 microns to be compressed into a final state of 46 microns, the thickness of the compressed state would be 0.32 times that of the original uncompressed state.

The shape of the coiled polypeptide chain which forms the enzyme or the antibody is critical to its function as an organic catalyst. Many, if not all, enzymes and antibodies are shape-selective. That is, they recognize specific reagents which have shapes that complement the shape of the coiled peptide chain. If the peptide chain becomes uncoiled or changes its shape and loses its specificity toward certain reagents, the protein is said to be denatured. To avoid denaturing the protein, it is necessary to avoid subjecting the protein to extreme heat or cold, to gross changes in pH, to harsh chemicals, and to dehydration. In many cases, it is desirable to keep biologically active proteins in contact with an aqueous liquid phase at all times.

It is within the scope of the present invention to form the compressed carrier substrate by compressing the uncompressed carrier after the enzyme has been covalently attached and while the enzyme is in contact with a stabilizing liquid phase. Additionally, when choosing a method of attachment for the enzyme, harsh chemicals and chemicals which fail to wash freely from the substrate should be avoided in order to minimize the possibility of such chemicals later denaturing the enzyme. One of the surprising features of the instant invention was the discovery that compressed membranes containing active immobilized enzyme could be ultrasonically welded and solvent welded without denaturing the enzyme.

Several means of immobilizing biologically active material on solid carriers are known, such as adsorption, ionic bonding, entrapment, and covalent bonding. Any such method which does not denature the enzyme antibody or other biologically active material be attached can be used in the present invention. Biologically active materials include proteins, enzymes, antigens, enzyme-antigen conjugates, enzyme co-factors, and nucleic acid derivatives. Examples of enzyme co-factors which may be employed with the invention are nicotine adenine dinucleotide phosphates (NAD and NADH).

Proteins, of which enzymes and antibodies are subclasses, are relatively large molecules that contain positively changed, negatively charged, and uncharged (non-ionic) portions. Ionicly bound° proteins can be produced when a charged portion of the protein comes in close contact to an oppositely changed portion of a solid carrier surface. Under many conditions this attachment is irreversible. Adsorptively bound proteins can be produced when the uncharged portion of the protein comes in close contact to an uncharged, non-ionic portion of a solid carrier surface. Several ionic and adsorptive attachments may be necessary to irreversibly bind a single protein.

Covalent bonds that immobilize enzymes are formed by linking amino groups or carboxyl groups, which are present in every enzyme, with polar functional groups attached to the membrane. The functional groups can be derived from components normally present in the material that forms a substrate of the membrane or the functional groups can be added to the substrate. Suitable functional groups include carboxyl groups, amino groups, sulphonic acid groups, imino groups, thio groups, hydroxyl groups, azo groups, epoxy groups, aldehyde groups, acid chloride groups, activated carbonyl groups, pyridyl groups, and phosphoryl groups. The functional groups may be further activated by chemical treatment to enhance their ability to join with the amino or carboxyl groups present in the enzyme molecules.

Virtually any enzyme can be covalently bonded to the carrier substrate. Examples of enzymes that may be covalently bonded are glucose oxidase, urease, creatinine deiminase, alcohol oxidase, glutamate oxidase, lactate oxidase, lysine oxidase, leucine dehydrogenase, sarcosine oxidase, creatinine amidohydrolase, creatinine amidinohydroxolase, trypsin, glutamate dehydrogenase, lactate dehydrogenase, and hexokinase. Good results have been obtained with glucose oxidase, urease, and creatinine deiminase. The nature of the reactants will dictate which enzymes should be utilized.

In a preferred form of the invention, the covalent bond is prepared by hydrolyzing peptide bonds which exist in nylon polymers. Aqueous acid solutions such as aqueous hydrochloric acid can hydrolyze the bond. The result is a nylon matrix having an amine group which can be further extended by attaching a bifunctional molecule such as glutaraldehyde. Attachment of the bifunctional molecule will leave a terminal carbonyl group which can form a covalent bond with the amino group of an enzyme.

Especially preferred carrier substrate materials are commercially available, reactivated, polyvinylidine difluoride membranes such as an Immobilon ™ AV affinity membrane available from Millipore of Waltham, MA, and a Immunodyne ™ membrane available from Pall of Glen Cove, NY.

It is possible to manufacture membranes containing a relatively high concentration of polar functional groups by casting a polymer membrane, such as a polyamide membrane, while simultaneously casting a surface modifying polymer having functional polar groups in abundance. Useful surface modifying polymers for this purpose are polymers containing substantial proportions of ionizable, acidic functional polar groups. Illustrative examples are carboxyl, sulphonic, phenolic, amino, thio carbonyl, phosphene, and phosphoryl groups. The instant invention can be applied to such surface-modified polymer membranes, irrespective of the method of introduction of the functional groups.

An essential part of the present invention is a reliable seal which prevents electrolyte solution from bypassing the enzyme membrane. It is recommended that this seal be made by welding the membrane directly to the housing. In the case of a circular membrane, the circumferential edge of the membrane should be welded to the housing. Alternately, the entire periphery of a membrane which is not circular should be welded to the housing. The term "welding" as applied here to a thermoplastic material is intended to encompass dielectric welding, high-frequency welding, hot-gas welding, induction welding, and ultrasonic welding. Of these, ultrasonic welding is preferred.

Basically, ultrasonic welding involves converting standard electrical energy at 50 or 60 cycles per second into mechanical energy of approximately 20,000 or 40,000 cycles per second. Methods of accomplishing this conversion are well known. The mechanical energy is transferred to a horn. For this purpose, a horn is a metal element which is shaped to fit closely against a surface of one of the items which are to be welded together. As the surface pressed against the horn vibrates in response to high-frequency mechanical energy, one or more other surfaces of the item are firmly held to prevent movement. The item between the vibrating and non-vibrating surfaces flexes at a high cyclic rate and generates heat through internal friction which melts portions of the item in a controlled manner. When the desired melting has occurred, the flow of mechanical energy is stopped and the melted parts are allowed to cool and solidify. The horn may, optionally, be shaped to mechanically cut away excess portions of membrane at the end of the welding process.

In accordance with the present invention, it is highly desirable to employ an energy director in the ultrasonic welding step in order to limit the amount of energy transferred to the injection molded pins. An energy director is a triangular projection which is either added to the item being welded or to the horn itself which focuses mechanical energy, particularly into one small area of a joint. The excess melted material from this one small area can flow uniformly around the periphery of the joint and produces a superior weld without unnecessarily interfering with the previously existing seal between the housing and the injected molded pin.

In the absence of a welding process such as one of those described above, it is possible to attach the membrane to the housing by means of a solvent cement adhesive. For particular combinations of housing material and membrane material, such a solvent cement attachment may result in an acceptable weld. However, in the majority of cases, the application of solvent cement to thermosetting plastic material will produce an unacceptably weak bond. For instance, Teflon, which is a possible choice for the housing of the present invention, has no acceptable solvent cement. On the other hand, acrylic plastics are known to have effective solvent cements, such as methylene chloride and ethylene dichloride and may be reliably attached to polyamide membranes to polyamide housings by the solvent cementing process.

In assessing the suitability of such solvent cementing techniques, one must consider the material of both the housing and the membrane. Where a reliable solvent is not known, ultrasonic welding is the recommended and preferred attachment procedure. Solvent cement systems producing bonds having strengths of about 90% or more as compared to the original thermosetting material are within the scope of the claims.

In most cases, the membrane will be located very near to the blocking membrane or the isolating organic matrix layer. One would still expect some of the solvent to pass through the membrane and infiltrate the space between the layer and the membrane. In addition, it is sometimes desirable to place an ionophore gel layer in the space between the membrane and the organic matrix layer to assist the migration of ions to the organic matrix layer. When utilized, the ionophore gel layer should completely cover the exposed surface of the organic matrix and be in physical contact with the compressed membrane.

Whether the inclusion of an ionophore gel layer is necessary depends on the particular catalyzed reaction products which are expected to form within the membrane. As an illustration, when the immobilized enzyme is glucose oxidase and the reagent is glucose, hydrogen peroxide will be produced which needs no assistance in migrating to a surface where it can be oxidized. In contrast, when the immobilized enzyme is urease acting upon a molecule of urea to produce one molecule of carbon dioxide and two ammonium ions, the presence of an ionophore layer containing an ionophore such as nonactin is essential. Other examples of useful ionophores are valinomycin to facilitate the transport of potassium ions, nonensin to facilitate sodium ion transport, and tridodecylamine to facilitate the transfer of hydrogen ions.

When an ionophore layer is employed, it is preferred that the ionophore be present in the form of an ionophore gel. An example of a useful ionophore gel is the gel containing about 1.5 weight percent nonactin, about 23 weight percent polyvinyl chloride, and about 75.5 weight percent dibutyl sebacate. This particular ionophore gel is conveniently applied when dissolved in tetrahydrofuran solvent. The solvent may be removed by simple drying. Dibutyl sebacate acts as a plasticizer for the ionophore gel, allowing it to be built up in the form of a thin flexible membrane. The ionophore gel layer may be built up by performing multiple application and drying steps.

A blocking layer may optionally be employed as a component of the claimed device. The blocking layer may be a membrane installed between the membrane containing biologically active material and the pin or other means for conducting electrical current in order to screen out chemical species which might interfere with the intended electrical signal. Alternatively, the blocking layer may be a coating, such as an electropolymerized polymer film, which accomplishes the same purpose. It may be employed whether an ionophore gel layer is present or not. Generally, a blocking layer is located so as to directly contact and completely cover the head of the pin or the organic matrix layer surface. If no ionophore gel is present, it is preferred that the blocking layer contact the membrane containing biologically active material.

A blocking layer having relatively few and relatively small pores is capable of preventing relatively low molecular weight compounds, as compared to the desired reaction products, from reaching the organic matrix layer or pin. For example, a non-porous cellulose acetate membrane could be placed over the platinum-coated pin to prevent ascorbic acid from reaching the organic layer when the desired reaction product is gluconolactone. Hydrogen peroxide from the oxidation of glucose would freely pass through the cellulose acetate membrane.

In some embodiments, the claimed device includes a protecting membrane through which the electrolytic sample solution must pass in order to reach the protein-carrying membrane. The protecting membrane extends completely across well or passage. It is preferred that the protecting enzyme membrane be permanently sealed to the housing by ultrasonic welding. The protecting membrane may be within the well or it may extend over the first aperture. It is preferred that the protecting membrane be flush with the external surface of the first aperture to present a simple flow profile to sample flow moving across the first aperture. The simple flow profile increases the tendency of the sample flow to move in plug flow fashion and thus decreases apparent response time and recovery time for the device when in contact with a flowing sample. Such a tendency toward plug sample flow makes the claimed device especially suitable for use in automatic analyzing systems which employ programmed switching of sample and purge flows.

As an illustrative example, a polycarbonate membrane would be a suitable protecting membrane for the device when it is used to sample the urea content of a spent dialysate produced by peritoneal dialysis. Such a protecting membrane would have a thickness of about 8 microns and would possess micropores having an effective pore diameter of approximately 300 Å. A membrane that meets these specifications may be obtained from Nucleopore Filtration Products of Pleasanton, CA., under the trade name Nucleopore TM. The protecting membrane is useful to prevent relatively high molecular weight interfering compounds from reaching the enzyme membrane and for protecting the enzyme membrane from contact with particulate foulant.

EXAMPLE 1

Figure 2:
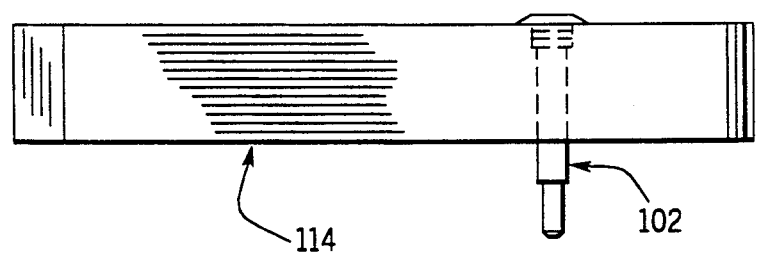

To further disclose the present invention, a reusable biosensor device 100 and a method for manufacturing the device are now described with reference to the identifying numerals employed in FIGS. 1 through 3. The biosensor device 100 is suitable for use as a potentiometric sensor. FIG. 1 is a plan view of the device 100 which includes a housing 114. The housing may be attached to a planar membrane, which is better illustrated in FIG. 3 as element 123, for particular applications. FIG. 2 is an elevation view of the device 100 depicting a pin 102 which passes substantially through and protrudes from the housing 114.

Figure 3:
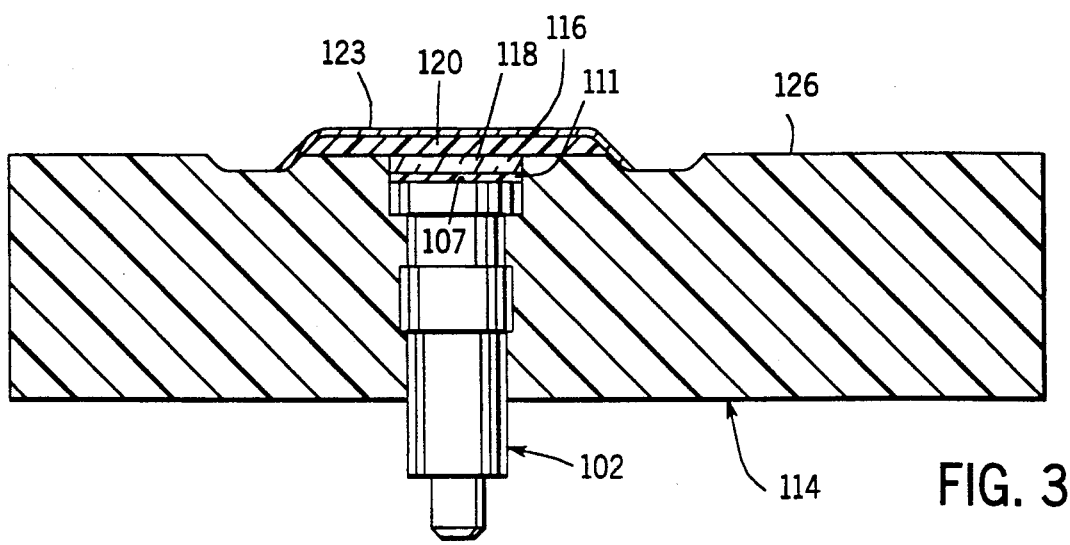
FIG. 3 is an enlarged cross-sectional view taken along the plane 3—3 in FIG. 1.

Referring now to FIG. 3, the head or receiving surface 107 of a metal pin 102 was coated with graphite ink to form an organic matrix 111 and cured at 120° C. for 30 minutes. Then, a thermoplastic polymer material, Zylon 90 TM, was injection-molded around the coated pin 102 in order to form a housing 114.

The pin 102 was placed in the mold so that the head, also called receiving surface 107, was located approximately 0.003 of an inch below a planar surface 126 which formed a boundary for a well 116 defined by the housing 114. The receiving surface 107 of the pin was 0.046 of an inch in diameter. An energy director (not shown) having a diameter of about 0.12 inch was cut into the housing around the pin 102. About 0.2 microliter of ionophore solution was dispensed into the well 116 on top of the pin 102 and allowed to dry for 10 minutes.

The ionophore solution contained 6.44 milligrams nonactin, 101.6 milligrams of polyvinyl chloride, 336.0 milligrams of dibutyl sebacate, and 2 milliliters of tetrahydrofuran. When the ionophore solution had dried, an ionophore gel 118 remained in the well 116. Two more applications of ionophore solution of similar size were made to build up the ionophore gel 118 to a desired thickness. After each application, the ionophore solution was allowed to dry for 10 minutes.

Urease enzyme was immobilized in a commercially available polyvinylidine difluoride reactivated membrane to produce an enzyme membrane 120. Specifically, 77.1 milligrams of urease enzyme was dissolved in 1,800 microliters of 0.5 molar potassium phosphate buffer solution (pH 7.4). The solution was applied to a Millipore Immobilon AV Affinity ™ membrane having a surface area of about 125 cm² on each sheet side, allowed to dry for 12 hours, and rinsed several times in a buffer solution having a pH of 7.5. This procedure is believed to have immobilized up to 25 international units of urease enzyme per cm² of membrane sheet surface as measured on one side. An international unit (IU) of an enzyme is defined as the amount of enzyme that produces one micromole of a reaction product in one minute under defined reaction conditions. The urease employed in this procedure contained about 182 international units per milligram of enzyme.

A portion of the enzyme membrane 120 was placed over the ionophore gel 118 and ultrasonically welded to the thermoplastic housing 114.

EXAMPLE 2

A biosensor device according to the present invention was constructed which included the device described in EXAMPLE 1. A path for flow across the biosensor device was established by placing a compressible gasket on the housing and clamping a flat top piece with an inlet and an outlet leading to the ends of the compressible gasket over the gasket. A flow of buffer solution was established through this flow path by pumping buffer solution at a rate of 475 microliters per minute through the flow path using a peristaltic pump. The outlet from the stream was connected to a flowing liquid junction reference electrode consisting of a silver chloride coated silver wire immersed in a flowing stream of 2 molar potassium chloride solution. The potential of the metal pin in the device was measured in relation to the reference electrode.

Diffusion resistance testing was conducted in flow-injection mode. That is, flow of a buffer solution was maintained continuously through the liquid side of the sensor cell. At intervals, reagent-rich buffer solution was also injected into the flow cell. Throughout the experiment, a steady flow of 475 microliters per minute was maintained through the flow cell. Injections of reagent solution were made in volumes of 100 microliters each. The voltage difference between the metal pin of the device and the flowing liquid junction reference electrode was recorded on a strip chart recorder. After each injection, the electrical signal was allowed to return to equilibrium before another injection of reagent-rich buffer solution was made.

The strip chart recorder so connected produced a reproducible peak having a maximum height which corresponded to a maximum voltage difference across the detector. Response time was calculated as the time from the solution injection to the time at which the maximum peak height was recorded. The width of the observed peak measured at one-half the maximum height was also observed and recorded. Finally, recovery time was defined to be the period of time necessary for the peak to return to 5% or less of maximum peak height as measured from the time of reagent-rich solution injection.

Figure 4:
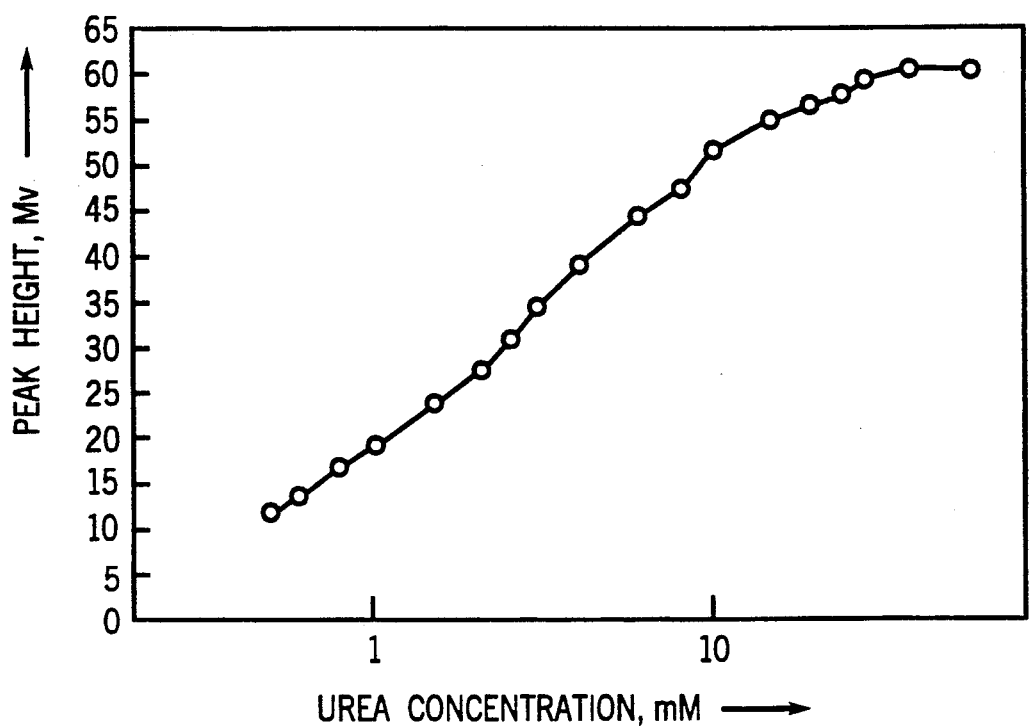
FIG. 4 is a graph of the electrical potential observed across an embodiment of the present invention as a function of the urea concentration in a flowing solution to which the embodiment was exposed.

The results recorded for a flowing pulse sample of urea when exposed to the urease enzyme membrane in the device are presented graphically in FIG. 4. This data shows that the device is capable of analyzing urea in aqueous solution with good resolution and a high degree of linearity.

EXAMPLE 3

The device described in EXAMPLE 2 was also tested using a stopped flow method. This experiment utilized the same apparatus as in EXAMPLE 2 above, but now buffer solution flow was interrupted by 10 seconds of reagent-rich sample flow followed immediately by a period of time during which sample and buffer flow through the device was completely stopped. The rate of change of the potential difference between the device and the reference electrode was monitored over a period of 10 seconds with no flow. Several different concentrations of urea solution were employed. The results are presented as FIG. 5.

Figure 5:
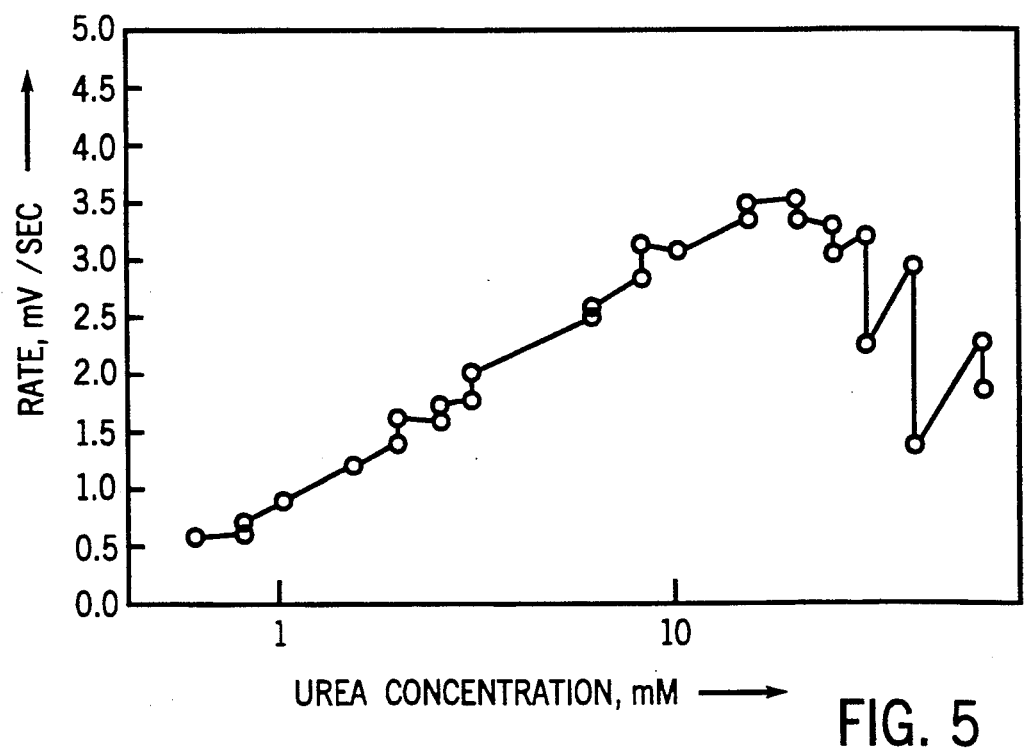
FIG. 5 is a graph of the rate of change of the electrical potential observed across an embodiment of the present invention as a function of the urea concentration in a stagnant solution to which the embodiment was exposed.

The data in FIG. 5 demonstrates that the device responds quickly when exposed to a change in urea concentration.

EXAMPLE 4

Figure 6:
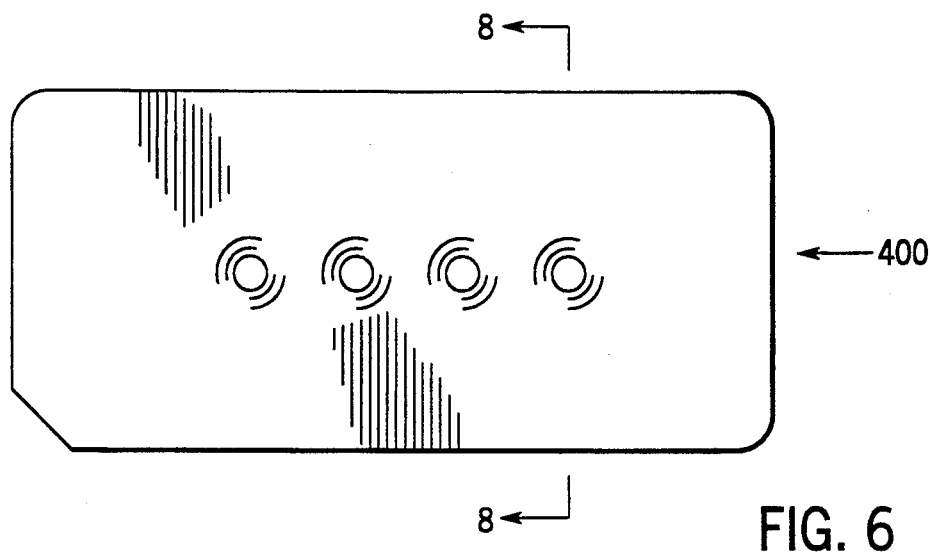
FIG. 6 is a plan view of a second embodiment of the present invention.
Figure 7:
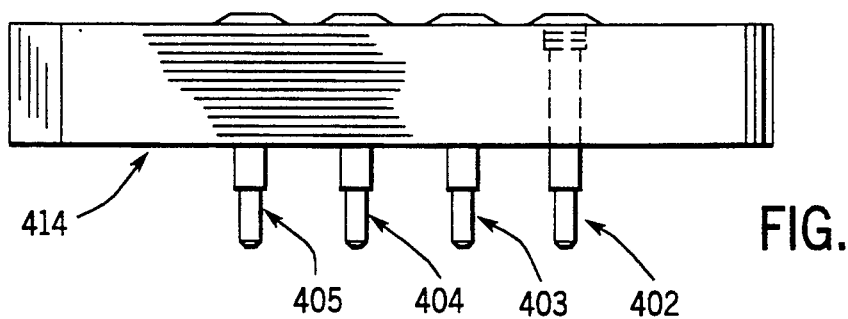
FIG. 7 is an elevation view of the device of FIG. 6.
Figure 8:
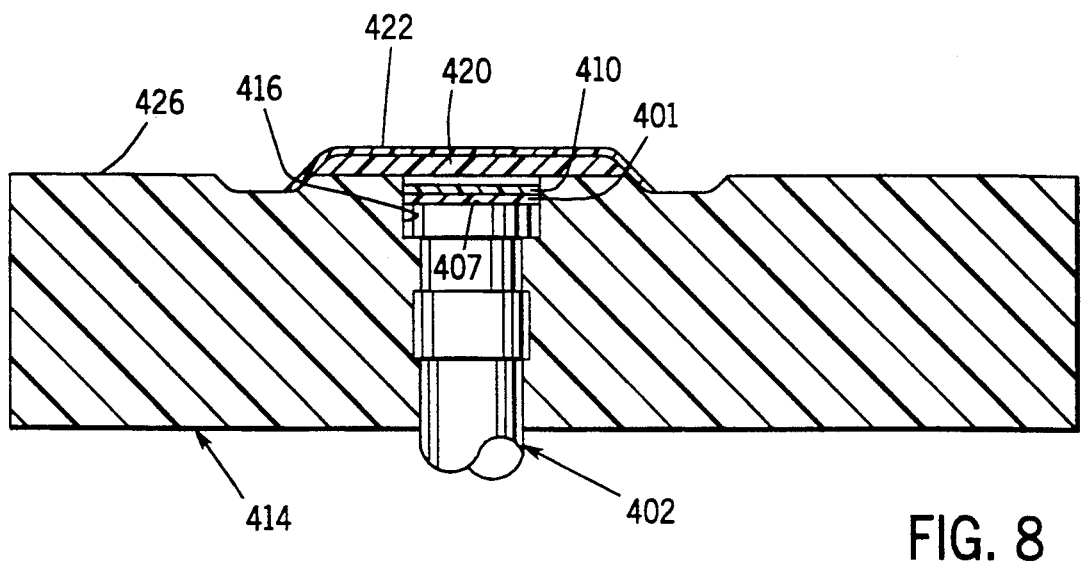
FIG. 8 is an enlarged cross-sectional view taken along the plane 8—8 of FIG. 6.

In this example, an amperometric glucose sensor apparatus 400 was prepared. The completed apparatus 400 is depicted in FIGS. 6 through 8. FIG. 6 is a plan view of the device 400 including a housing 414 to which a protecting membrane, better illustrated in FIG. 8 as element 422, may optionally be attached for particular applications. FIG. 7 is an elevation view of the device 100 which shows a pin 402 passing substantially through and protruding from the housing 414.

Referring now to FIG. 8, heads 407 of two metal pins 402 and 403 were coated with platinum by sputtering with platinum under a vacuum for several hours until a coating 401 of about 2 micrometers of platinum was deposited. The head of a third metal pin 404 was coated with silver by sputtering silver under a vacuum for several hours until a layer of about 2 micrometers of silver was deposited. The head of the pin 404 was then chloridized by placing the pin in a solution of 5 mL bleach containing 0.3 gram sodium chloride and 0.3 gram disodium hydrogen phosphate for 10 to 20 seconds. A fourth pin 405 was an uncoated pin.

The pins 402–405 were placed in a mold (not shown). Then a thermoplastic polymer material, Zylar 90 ™ obtained from Polysar of Madison, Connecticut, was injection-molded around the pins in order to produce a housing 414. The pins were placed in the mold so that the heads 407 of the metal pins 402–405 were located approximately 0.003 of an inch below a planar surface 426, thereby forming a well 416 defined by the housing 414. The heads 407 of the pins were 0.046 of an inch in diameter. The top approximately 0.002 inch of the housing 414 was milled away to bring the planar surface 426 nearer to the heads of the pins, in order to decrease the thickness of a diffusional layer. An energy director (not shown) having a diameter of about 0.12 inch was cut into the housing around the pin 402.

Glucose oxidase enzyme was immobilized in a commercially available polyvinylidine difluoride reactivated membrane to create an enzyme membrane 420. Specifically, 86.9 milligrams of glucose oxidase enzyme was dissolved in 4866 microliters of 0.5 molar potassium phosphate buffer at a pH of 7.5 to produce a solution. Eighteen hundred microliters of the solution was applied to a Millipore Immobilon AV Affinity ™ membrane having a surface area of about 125 cm² on each side. The enzyme membrane 420 was allowed to dry for four hours and twenty minutes, and then rinsed several times in a buffer solution having a pH of 7.5.

This procedure is believed to have immobilized up to 28.8 international units of urease enzyme per cm² of membrane sheet surface as measured on one side. An international unit (IU) of an enzyme is defined as the amount of enzyme that produces one micromole of a reaction produce in one minute under defined reaction conditions. The glucose oxidase employed in this procedure contained about 112 international units per milligram of enzyme.

The enzyme membrane 420 containing immobilized glucose oxidase was subsequently compressed in order to decrease the effective diffusion resistance of the enzyme membrane toward glucose. This was accomplished by physically pressing the enzyme membrane 420 between two flat inelastic surfaces with a pressure of 3.5 tons per cm² for 3 minutes while the enzyme membrane was wet with buffer. In its compressed state, the enzyme membrane 420 had a thickness of 0.0040 inch, significantly less than the thickness before compression which was 0.0052 inch. The enzyme membrane 420 was placed over the pin 402, and ultrasonically welded to the thermoplastic housing 414. The protecting membrane 422 may be placed over the enzyme membrane 420, if desired.

A path for flow across the sensor device was established by placing a compressible gasket (not shown) on the housing and clamping a flat top piece (not shown) with an inlet and an outlet over the gasket. A flow of buffer solution was established through this flow path by pumping buffer solution at a constant rate of 485 microliters per minute through the flow path using a peristaltic pump. The four pins 402–405 were located in a row, with the pin 402 at one end of the row and the pin 405 at the other end. The direction of the flow was from the pin 402 towards the pin 405. The potential of the pin 402 was kept 650 millivolts more positive than that of the pin 404 by use of a potentiostat. Pin 405 was used as a counter electrode, so current generated (by holding the pin 402 at 650 mV) flowed between the pins 402 and 405. The flow of current between the pins 402 and 405 was measured with an amperometric detector.

Diffusion resistance testing was conducted in flow-injection mode. That is, flow of a buffer solution was maintained continuously through the liquid side of the apparatus 400. At intervals, glucose-rich buffer solution was also injected into the flow cell. Throughout the experiment, a steady flow of about 485 microliters per minute was maintained through the flow cell. Injections of glucose-rich solution were made in volumes of 100 microliters each. The flow of current between the pins 402 and 405 of the device was recorded on a strip chart recorder. After each injection, the electrical signal was allowed to return to equilibrium before another injection of glucose-rich buffer solution was made. Measurements were made in a similar manner with 0.1019 mM hydrogen peroxide (H2O2), 2.211 mM glucose, 0.221 mM ascorbic acid (AA) and 1.185 mM 4-acetamidophenol (APAP).

Preparation of "Coated" Sensor with Blocking Layer

A blocking layer 410 was formed by electropolymerization over the pin 402 using the following procedure. A monomer solution was prepared by dissolving 0.18855 gram of 1,2-diaminobenzene and 0.18866 gram of 1,2-dihydroxybenzene in 500 mL of buffer. The buffer had been prepared previously, by mixing 16 grams NaCl, 0.403 gram KCl, 4.29 grams disodium hydrogen phosphate pentahydrate, and 0.4084 gram potassium dihydrogen phosphate in 2 liters of water. The buffer had a pH of 7.5.

The monomer solution was pumped through the flow cell at 485 microliters per minute for 18.5 hours while the potential of the pin 402 was cycled at 2 millivolts per second between 0 and 800 millivolts, relative to the pin 404. Then, solid 1,2-diaminobenzene and 1,2-dihydroxybenzene was added to the monomer solution to bring the concentration to a total of 0.18 molar and 0.20 molar 1,2-diaminobenzene and 1,2-dihydroxybenzene, respectively. The potential cycling was thereafter continued for an additional 7.2 hours.

Measurements were made in the flow injection mode described above. Flow was maintained at 485 microliters per minute. Measurements were taken after injecting 100 microliter samples of 0.1019 mM hydrogen peroxide, 2.211 mM glucose, 0.6391 mM ascorbic acid (AA), 5.645 mM ascorbic acid (AA), and 10.08 mM 4-acetamidophenol (APAP). The higher concentrations of AA and APAP were used to produce a more easily measurable signal.

A strip chart recorder connected to the amperometric detector produced a reproducible peak having a maximum height which corresponded to a maximum current through the detector. Response time (t max) was calculated as the time from analyte-rich solution injection to the time at which the maximum peak height was recorded. Response time (t 1st) was calculated as the time from the analyte-rich solution injection to the time at which the first detectable change in amperometric current was measured. Finally, recovery time (t 95%) was defined to be the period of time necessary for the peak to return to 5% or less of the maximum peak height as measured from the time of test substance-rich solution injection. The response and recovery times observed are set forth in TABLE 4A. Corresponding selectivities are presented as TABLE 4B.

TABLE 4A

| Response and Recovery Times of Device Containing Glucose Oxidase Membrane | | | |
|---|---|---|---|
| Compound | t max | t 1st | t 95% |
| Uncoated Sensors | | | |
| H2O2 | 31.6 | 8 | 72 |
| Glucose | 33.1 | 10.2 | 93.6 |
| AA | 36.2 | 10 | 127 |
| APAP | 46.4 | 12 | 146 |
| Coated Sensors | | | |
| H2O2 | 31.7 | 10 | 75.6 |
| Glucose | 41.3 | 12.8 | 103 |
| AA | 26.6 | — | 60 |
| APAP | 25 | 9 | 42 |

Key to Abbreviations:
AA is ascorbic acid
APAP is 4-acetamidophenol
H2O2 is hydrogen peroxide The response times in TABLE 4A indicate that an embodiment of the present invention containing glucose oxidase responds quickly to changes in the glucose concentration of a flowing sample stream and recovers rapidly when conditions return to their previous state. The results also indicate that the electropolymerized film coating does not substantially increase the response and recovery times of the sensor to glucose.

TABLE 4B

Selectivity of Device Containing Glucose Oxidase Membrane

| Compound | Response nA/mM | Relative Response % |
|---|---|---|
| $H_2O_2$ | 256 | |
| Glucose | 50.4 | 20* |
| AA | 3.39 | 6.7 |
| APAP | 1.10 | 2.2 |
| AHB | <0.05 | <0.1 |
| GT | 0.15-0.9 | 0.3 |
| SALA | 3.37-1.82 | 6.7 |
| Uric Acid | 1.05 | 2.12 |
| GA | 2.18-1.5 | 4.3 |
| Py | 4.61-3.2 | 9.2 |
| DOPA | 4.53 | 9.0 |

*relative to $H_2O_2$, all other compounds relative to glucose
Key to Abbreviations:
AA is ascorbic acid
APAP is 4-acetamidophenol
$H_2O_2$ is hydrogen peroxide
AHB is 4-amino-2-hydroxybenzoic acid
GT is gentisic acid
SALA is salicylamide
GA is guaiacol
PY is pyrocatechol
DOPA is L-beta-3,4-dihydroxyphenylalanine The relative selectivities shown in TABLE 4B indicate that the device generates a relatively strong signal for hydrogen peroxide and is relatively immune from background interference from several known interfering agents.

The test results for peak height responses of the coated and uncoated sensor are shown in TABLE 4C.

TABLE 4C

| | Peak Heights | | | |
|---|---|---|---|---|
| | Hydrogen Peroxide nA/mM | Glucose nA/mM | AA nA/mM | APAP nA/mM |
| Uncoated Sensor (no blocking layer) | 290.8 | 63.4 | 84.2 | 113.9 |
| Coated Sensor (with blocking layer) | 179 | 29.3 | 1.93 | 0.0566 |

Inspection of TABLE 4C reveals that response of the sensor coated with a blocking layer to ascorbic acid (AA) and 4-acetamidophenol (APAP) is decreased dramatically, as compared to the uncoated sensor. The response for 4-acetamidophenol (APAP) is less by a factor of more than 2000 when the blocking layer is employed. The decrease in response is accompanied by an increase in the selectivity of the sensor.

The sensor was stored for several weeks at room temperature in pH 7.5 buffer. The response of the electrode to glucose relative to the hydrogen peroxide ($H_2O_2$) response was found to remain fairly constant over this time period. The selectivity of the sensor, however, decreased with time. The relative response ratios for glucose and APAP with respect to hydrogen peroxide over the period of time are presented as TABLE 4D.

TABLE 4D

| Day | Glucose/H2O2 × 100 | APAP/H2O2 × 100 |
|---|---|---|
| 1 | 16.4 | 0.032 |
| 1 | 22.7 | 1.34 |
| 10 | 24.1 | 3.07 |
| 16 | 24.9 | 3.4 |
| 55 | 20.9 | 63 |

EXAMPLE 5

Samples of a membrane containing immobilized urease, prepared according to the procedure described in EXAMPLE 1, were compressed in order to decrease the effective diffusion resistance of the membrane toward urea. This was accomplished by physically pressing the membrane between two flat inelastic surfaces with a pressure of 1.0 to 1.5 metric ton per square centimeter for about 3 minutes. The membrane thicknesses decreased from an original 0.00525 inch to between 0.00295 and 0.00325 inch. A portion of the compressed enzyme membrane sample was placed over an ionophore gel layer and ultrasonically welded to a thermoplastic housing surface.

A biosensor device was constructed in the following manner. A flow path across the sensor device was established by placing a compressible gasket on the housing and clamping a flat top piece with an inlet and outlet leading to the ends of the compressible gasket over the gasket. A flow of buffer solution was established through the flow path by pumping buffer solution at a constant rate of about 950 microliters per minute through the flow path using a peristaltic pump. The outlet from the stream was connected to a flowing liquid junction reference electrode consisting of a silver chloride coated silver wire immersed in a flowing stream of 2 molar potassium chloride solution. The potential of the metal pin in the device was measured in relation to the reference electrode.

Diffusion resistance testing was conducted in flow-injection mode. That is, flow of a buffer solution was maintained continuously through the liquid side of the sensor. At intervals, urea-rich buffer solution was also injected into the flow cell. Throughout the experiment, a steady flow of about 950 microliters per minute was maintained through the flow cell. Injections of urea-rich solution were made in constant volumes of about 40 microliters each. The voltage difference between the metal pin of the device and the flowing liquid junction reference electrode was recorded on a strip chart recorder. After each injection, the electrical signal was allowed to return to equilibrium before another injection of urea-rich buffer solution was made. The results are shown in TABLE 5A.

TABLE 5A

| Urea Concentration (mg Urea Nitrogen per Deciliter) | Peak Height (mV) |
|---|---|
| 13.92 | 15.7 |
| 27.72 | 23.4 |
| 54.91 | 31.7 |
| 81.56 | 35.9 |
| 107.69 | 39.0 |
| 13.92 | 16.3 |

A linear least squares fit of the data presented in TABLE A produces the following correlating equation, with a correlation coefficient of 0.9996:

Peak Height $(mV) = \log(mg$ urea nitrogen per deciliter$) - 13.8389$.

Urea-rich dialysate was collected from a patient on continuous peritoneal dialysis. A patient was infused with 2000 mL of Delfex ™ (Baxter) 1.5% Dextrose containing 538 mg% sodium chloride, 448 mg% sodium lactate, 25.7 mg% calcium chloride, and 5.08 mg% magnesium chloride. Ten milliliter samples were collected from the patient immediately after infusion and at timed intervals. The urea concentration of the spent dialysate was calculated from the peak height and the correlating equation described above. The urea concentration of the spent dialysate samples was measured with Vision Testpacks ™ obtained from Abbott Laboratories for comparison. Typical results are shown in TABLE 5B.

TABLE 5B

| Dialysate Time in Patient (minutes) | Sensor Response Peak Height (mV) | mg Urea Nitrogen/dL | |
|---|---|---|---|
| | | Calculated from Sensor Response (mg Urea N/dL) | Vision Instrument (mg Urea N/dL) |
| 120 | 33.8 | 68 | 67* |
| 240 | 36.8 | 89 | 74** |
| 240 | 37.1 | 91 | 74** |
| 15 | 27.7 | 40 | 36 |
| 10 | 26.7 | 36 | 33 |
| 5 | 23.7 | 28 | |

*Sample concentration was out of range so sample was diluted 1 to 1 with buffer.
**Sample concentration was out of range so sample was diluted 1 to 1 with buffer. Value of single determination.

The data in TABLES 5A and 5B demonstrate that the device is capable of analyzing urea in physiological samples with good precision and accuracy.

Figure 9:
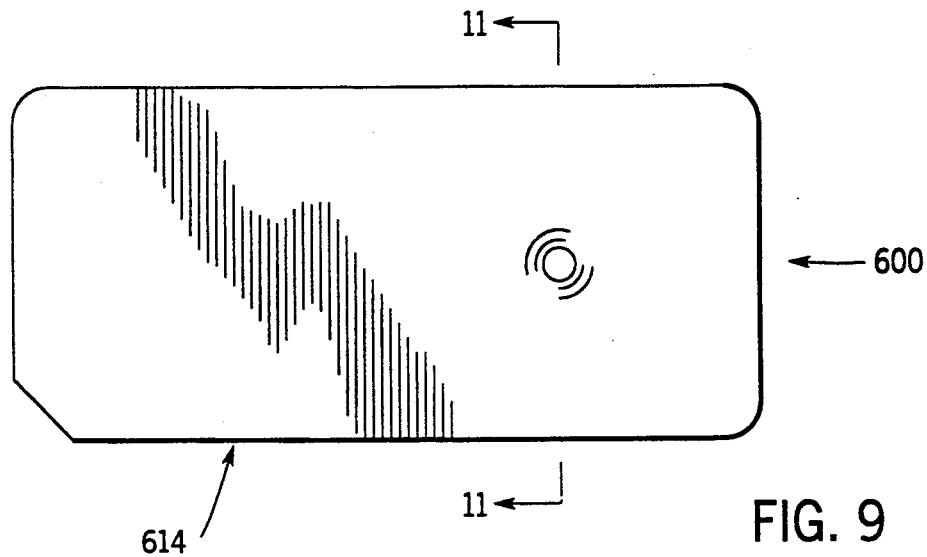
FIG. 9 is a plan view of a third embodiment of the present invention.
Figure 10:
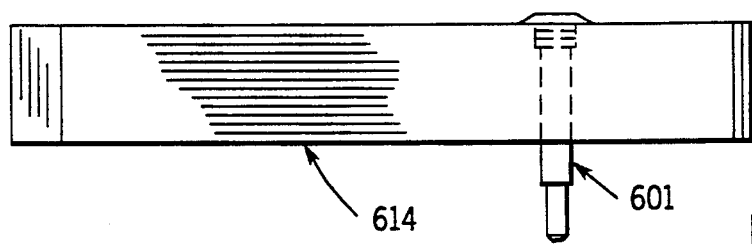
FIG. 10 is an elevation view of the device of FIG. 9.
Figure 11:
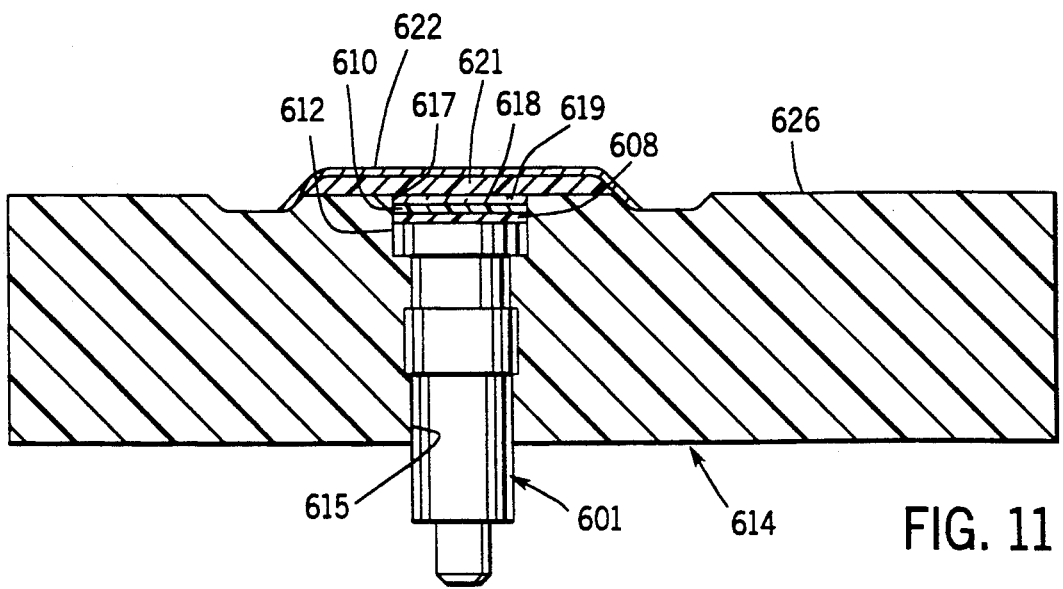
FIG. 11 is an enlarged cross-sectional view taken along the plane 11—11 of FIG. 9.

FIGS. 9 through 11 illustrate a device 600 according to the present invention which is suitable for use as either a potentiometric or an amperometric sensor. The device 600 includes a housing 614, shown in FIG. 9. FIG. 10 depicts a means for conducting electrical current 601 which protrudes into and passes substantially through the housing 614.

Referring now to FIG. 11, an organic matrix 608 extends across a passage 619 defined by the housing 614. For example, the organic matrix 60S may be a carbonaceous layer which coats a portion of the means for conducting electricity 601. The organic matrix 608 prevents analyte solution from contacting the means for conducting electricity 601, which is usually metallic, and thereby minimizes corrosion. The organic matrix 608 is an optional element of the present invention. Alternatively, the means for conducting electrical current 601 may be composed of or coated with corrosion resistant materials, such as platinum, palladium, and gold.

The passage 619 is defined by the housing 614 and forms a liquid-tight seal 612 adjacent the means for conducting electrical current 601. The passage 619 terminates in a first aperture 615 and a second aperture 617, also defined by the housing 614. A membrane 621 which contains an immobilized biologically active material, extends across the passage 619 near a planar surface 626, which is an external surface of the housing relatively far from the first aperture 615. An ionophore gel 618 is trapped in the passage 619 between the membrane 621 and the means for conducting electrical current 601.

A blocking layer 610 may, optionally, extend across the passage 619 between the membrane 621 and the means for conducting electrical current 601 to prevent low molecular weight interfering species from reaching the means for conducting electrical current 601. A protecting membrane 622 may optionally abut the planar surface 626 and cover the membrane 621.

Although the invention has been illustrated by the preceding examples, it is not to be construed as being limited to the examples employed herein. Various modifications and embodiments can be made without departing from the spirit and the scope of the claims.

WHAT IS CLAIMED IS:

1. A device for measuring the concentration of an analyte in a solution, which comprises:
   (a) an electrically insulating housing which describes a first aperture, a second aperture, and a passage that extends from the first aperture through the housing to the second aperture and which is impervious to a solution that contains an analyte selectively catalyzed by an enzyme;
   (b) means for conducting electrical current which extend through the first aperture into the passage and are sealed against the first aperture in a manner that prevents fluid flow; and
   (c) a membrane located across the passage and welded in place such that the solution must pass from the second aperture through the membrane in order to contact the means for conducting electrical current, said membrane having
   a substrate including an internal surface which defines a plurality of micropores distributed throughout the substrate;
   a plurality of functional groups attached to the internal surface of said substrate; and
   molecules of a biologically active material attached to at least a portion of the functional groups.

2. The device of claim 1 wherein the substrate exhibits a diffusion resistance which is less than the diffusion resistance exhibited by said substrate in an uncompressed state, with respect to the analyte which is catalyzed by the protein.

3. The device of claim 1 wherein the density of the substrate of the membrane in a compressed state is in the range of about 1.25 to about 5.0 times the density of the substrate in an uncompressed state.

4. The device of claim 2 wherein the substrate is compressed after the molecules of the protein are attached to the functional groups and the membrane is welded in place across the passage after the substrate is compressed.

5. The device of claim 1 wherein the substrate is a porous, membrane comprising a polyamide.

6. The device of claim 1 wherein the substrate is a porous membrane comprising polyvinylidine difluoride.

7. The device of claim 1 wherein the protein is glucose oxidase.

8. The device of claim 1 wherein the protein is urease.

9. The device of claim 1 wherein the protein is creatinine deiminase.

10. A reusable biosensor device for measuring the concentration of an enzyme-catalyzed reagent in solution, which comprises:
   (a) an electrically conducting pin having one or more side surfaces, a transmitting surface, and a receiving surface;
   (b) a nonporous, electrically insulating housing which is impervious to the solution, covers only the side surfaces, and extends beyond the side surfaces so as to define a well that is in fluid communication with the receiving surface;

(c) an ionophore gel inside the well which coats the receiving surface;

(d) an enzyme membrane containing an immobilized enzyme and located across the well, welded to the housing so that the enzyme membrane, the housing, and the receiving surface completely surround the ionophore gel and so that the solution must pass through the enzyme membrane in order to contact the ionophore gel; and (e) a substantially planar membrane which covers the enzyme membrane and presents a simple flow profile to the solution.

11. The device of claim 10 wherein the enzyme membrane is in a compressed state such that the density of the enzyme membrane in the compressed state is in the range of about 1.25 to about 5.0 times the density of the enzyme membrane in an uncompressed state.

12. The device of claim 11 wherein the enzyme membrane is ultra-sonically welded to the housing after the immobilized enzyme is attached to the enzyme membrane and after the enzyme membrane is compressed.

13. The device of claim 10 wherein said well contains an electrically conductive organic matrix which coats the receiving surface of the pin.

14. The device of claim 10 wherein a blocking layer extends across the well between the enzyme membrane and the receiving surface.

15. The device of claim 10 wherein the enzyme membrane is formed in the shape of a substantially flat and relatively thin sheet and wherein a relatively larger protecting membrane is welded to the housing and covers the enzyme membrane, trapping the enzyme member against the housing.

16. The device of claim 10 wherein the immobilized enzyme is disposed throughout the enzyme membrane in a substantially uniform distribution.

17. The device of claim 10 wherein the enzyme membrane has a thickness and in that the thickness in a compressed state is in the range of about 0.2 to about 0.8 times the thickness in an uncompressed state.

18. The device of claim 10 wherein the immobilized enzyme is urease.

19. The device of claim 10 wherein the immobilized enzyme is creatinine deiminase.

20. A device for measuring the concentration of an enzyme-catalyzed reagent in a solution, which comprises:

(a) an electrically conducting pin having sides and a receiving surface;

(b) a thermoplastic polymer molded housing which covers the sides of the pin but does not cover the receiving surface;

(c) an enzyme membrane having a compressed substrate having functional groups that are covalently attached to an immobilized enzyme, said enzyme membrane being welded to the housing and contacting the blocking layer, with the membrane, the pin, and the housing completely surrounding the receiving surface, whereby the enzyme-catalyzed reagent must pass through the enzyme membrane in order to contact the receiving surface; and (d) a substantially planar protecting membrane covering the enzyme membrane.

21. The device of claim 20 wherein the substrate is a porous membrane comprising polyvinylidine difluoride.

22. The device of claim 20 wherein a blocking layer extends across the receiving surface, between the receiving surface and the enzyme membrane.

23. The device of claim 20 wherein a layer of graphite ink coats the receiving surface.

* * * * *